US00PP14295P39

(12) United States Plant Patent
van Rijsselberghe

(10) Patent No.: US PP14,295 P3
(45) Date of Patent: Nov. 11, 2003

(54) PHALAENOPSIS PLANT NAMED 'ISIS'

(50) Latin Name: *Phalaenopsis hybrid*
Varietal Denomination: Isis

(75) Inventor: Ronie van Rijsselberghe, Lochristi (BE)

(73) Assignee: Microflor NV, Lochristi (BE)

( * ) Notice: Subject to any disclaimer, the term of this patent is extended or adjusted under 35 U.S.C. 154(b) by 0 days.

(21) Appl. No.: 10/090,773

(22) Filed: Mar. 6, 2002

(65) Prior Publication Data

US 2003/0172426 P1 Sep. 11, 2003

(51) Int. Cl.[7] ..... A01H 5/00
(52) U.S. Cl. ..... Plt./311

(58) Field of Search ..... Plt./311

(56) References Cited

PUBLICATIONS

UPOV–ROM GTITM, Plant Variety Database, 2002/05, GTI Jouve Retrieval Software, Citation for Phalaenopsis 'Isis'.*

* cited by examiner

*Primary Examiner*—Bruce R. Campell
*Assistant Examiner*—June Hwu
(74) *Attorney, Agent, or Firm*—Foley & Lardner

(57) ABSTRACT

A new and distinct cultivar of Phalaenopsis orchid named 'Isis' characterized by broad elliptic leaves; green/brown stem; showy light purple flowers with dark purple stripes, and white margins and bases; dull, green leaves; and freely flowering with 10–15 flowers and buds per raceme.

2 Drawing Sheets

Latin name of the genus and species of the plant claimed: Phalaenopsis hybrid.
Variety denomination: 'Isis'.

BACKGROUND OF THE INVENTION

The present invention comprises a new and distinct cultivar of Phalaenopsis orchid, hereinafter referred to by the cultivar name 'Isis'. The genus Phalaenopsis is a member of the family Orchidaceae.

Phalaenopsis comprises a genus of about 55 species of herbaceous perennials many of which, or the hybrids thereof, are suitable for cultivation in the home or greenhouse. Phalaenopsis is predominantly epiphytic or rock-dwelling, and is native to tropical Asia, Malay Archipelago and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

Phalaenopsis orchids, often referred to as 'Moth Orchids' in the horticultural trade, are frequently used to furnish cut flowers for the florist trade or sold as flowering potted-plants for home or interiorscape.

Phalaenopsis produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments.

Phalaenopsis orchids are typically propagated from seeds. Asexual propagation of Phalaenopsis is often done from off-shoots which frequently arise from the lower bracts of the inflorescence. The resulting plants are detached from the mother plant and may be planted in a suitable substrate.

The new cultivar is a product of a breeding program carried out by the inventor, Ronie van Rijsselberghe. The new cultivar is a result of a cross of two unnamed non-commercial varieties owned by the applicant made in September 1993. The new cultivar 'Isis' was selected from the progeny of the stated cross in Lochristi by the inventor in March 1996.

Asexual propagation by tissue culture, performed by the inventor in Lochristi, Belgium in March 1996, was used to increase the number of plants for evaluation and has demonstrated that the combination of characteristics as here in disclosed for 'Isis' are firmly fixed and are retained through successive generations of asexual reproduction. The new cultivar reproduces true-to-type.

BRIEF DESCRIPTION OF THE INVENTION

The following traits have been repeatedly observed to be characteristics which in combination distinguish 'Isis' from generally available seedling-derived Phalaenopsis common in commercial cultivation:

1. broad elliptic leaves;
2. green/brown stem;
3 showy light purple flowers with dark purple stripes, and white margins and bases;
4. dull, green leaves; and
5. freely flowering with 10–15 flowers and buds per raceme.

'Isis' has not been observed under all possible environmental conditions. The phenotype may vary significantly with variations in environment such as temperature, light intensity, fertilization and day length without any change in the genotype. The following observations, measurements and values describe plants grown in Lochristi, Belgium under a glass covered greenhouse in a 12 cm container under conditions which approximate commercial Phalaenopsis production conditions. Plants were grown for about 45 weeks after planting. During the first 25 weeks of production, day and night temperatures averaged 25 degrees Celsius; during the next four weeks of production, day and night temperatures averaged 18 degrees Celsius; and for the last weeks of production, day and night temperatures averaged 20 degrees Celsius. Lowest temperature tolerance is 15 degrees Celsius, highest is 38 degrees Celsius.

Perhaps the closest commercial comparison to 'Isis' can be made to 'Artemisa' (U.S. Plant Pat. No. 13,048). In side-by-side comparisons conducted in Rijswijk, The Netherlands, plants of the new Phalaenopsis have wider leaves. The leaves have a midrib which has the same colour as the rest of the leaf whereas the midrib of 'Artemisa' is dark purple. The leaves of 'Artemisa' are glossier than the leaves of 'Isis'. The underside of the leaf of 'Artemisa' is green with purple spots and a purple margin and midrib whereas the leaf of 'Isis' is green with a only a small purple margin, RHS 187A. The inflorescence stem of 'Artemisa' is darker than the inflorescence stem of 'Isis'. The flowers of 'Artemisa' are much darker purple than the flowers of 'Isis' which also have white margins and the base of the petals are white whereas the petals bases of 'Artemisa' are purple. The petals of 'Artemisa' are darker purple than the petals of 'Isis'. 'Artemisa' has a much shorter stem and starts producing flowers much lower on the stem (approximately 10 cm) than 'Isis'.

BRIEF DESCRIPTION OF THE DRAWING

The accompanying photographic drawings show typical plant and flower characteristics of 'Isis' with colors being as true as possible with drawings of this type. The photographs were taken approximately at noon on Dec. 28, 2001 in Rijswijk, The Netherlands.

The first drawing shows a 50-week old plant

The second drawing (left side) shows a comparison photo of a 50-months old plants of 'Isis' to the left and 'Artemisa' to the right.

The photo in the right upper corner shows a close-up comparison of 'Artemisa' (left) and 'Isis' (right).

The photo in the right lower corner shows a close-up of the leaves ('Isis' left and 'Artemisa' right).

DETAILED BOTANICAL DESCRIPTION

All color references are measured against The Royal Horticultural Society (R.H.S.) Colour Chart. Colors are approximate as color depends on horticultural practices such as light level and fertilization rate, among others, without, however any change in genotype.

Propagation: Asexual propagation by tissue culture.

Plant: Under appropriate growing conditions, plants attain a mature size of 60 cm in height and 35 cm in width.

*Vigor.*—Moderate.

Leaves:

*Form.*—The leaf blade shape is obovate with an obtuse to retuse apex and a cuneate base. The margins are entire. The midrib is furrowed. The leaf blade is smooth and leathery on both sides. The upper leaf surface is smooth, slightly furrowed and leathery. The leaves are smooth and very leathery.

*Size.*—Leaf blades of a mature-sized plant are 20 cm in length and 9.2 cm in width.

*Veins.*—Venation parallel, midrib furrowed, veins have the same color as the leaf blades, upper side green; in between RHS 137A and 146A (Yellow-green Group), under side yellow-green; varying between RHS 146A and RHS 146B.

*Color.*—Mature Leaf Upper surface: Green to yellow-green; from RHS 137A to 146A. Mature Leaf Lower surface: Yellow-green; varying between RHS 146A and RHS 146B, small purple margin, RHS 187A. Immature Leaf Upper surface: Green to yellow-green; from RHS 137A to RHS 146A. Immature Leaf Lower surface: Yellow-green; varying between RHS 146A and RHS 146B.

Inflorescence:

*Number of flowers per inflorescence.*—Average 14.

*Blooming season.*—January through March in Northern Europe.

*Lastingnes of blooms.*—Approximately two weeks.

*Blooms subject to fading.*—Average 14 days.

*Stem.*—65 cm average length, 6 mm average diameter; brown in color, RHS 200 A, with tiny greyed-green spots, RHS 191 B.

*Sepals.*—Shape: Broad elliptic. Description: 3 Sepals smooth, top obtuse to obtusely acute, base broad cuneate, margins entire. Upper Surface Color: Purple; varying between RHS 77C and RHS 77D, even lighter towards the margins. Markings (venation) darker: purple; RHS N78B. Lateral sepals have numerous dots at the base, average size 0.5 mm, purple in color; RHS N78A. Lower Surface Color: Purple; varying between RHS 77C and RHS 77D, lighter towards the margins. Markings (venation) darker: purple; RHS N78C. Size: average length 4 cm, average width 3 cm.

*Petals.*—Shape: 2 lateral petals reniform. Description: 2 lateral petals are smooth, top rounded, base broad acuminate. Upper Surface Color: Purple; RHS N78C becoming paler towards the margins RHS 69D, base RHS 69D, markings (venation) darker purple; RHS N78B. Lower Surface Color: Purple; from RHS 77B to RHS N78C becoming paler towards the margins RHS 69D, base RHS 69D, markings (venation) darker purple; RHS N78B. Size: (lateral petals) average length 4 cm, average width 4.8 cm.

*Labellum.*—Shape: Three-parted (lobed). Description: Lateral lobes rhomboidal/deltoid, top obtusely acute, dorsal lobe inverted deltoid, top cleft into two horn-like projections, which are twisted and curled. In the middle of the labellum (upper side), where the lobes meet, there is a small elevation, average height 4 mm, average width 5 mm, this elevation is cleft and almost two-parted. It is yellow in color; RHS 9B with greyed-purple dots and stripes (RHS 184A). Upper Surface Color: Purple; RHS N79C, lateral lobes more reddish-purple (RHS 72A), base white (RHS 155A), striped greyed-purple; RHS 184A. Lower Surface Color: Purple to red-purple; between RHS 72A and 72B to RHS N79C, lateral lobes white at the base (RHS 155A). Size: Lateral lobes: average length 2.1 cm, average width 1.5 cm, dorsal lobe: average length 2.4 cm, average width 2.1 cm, the horn-like projections have an average length of 1.8 cm (they are twisted and curled).

*Apex.*—Lateral lobes: obtusely acute, dorsal lobe cleft into two horn-like projections.

*Base.*—Lateral lobes cuneate, dorsal lobe acute.

*Raceme.*—Diameter: Average 11 cm. Height: Average 25 cm (measured from lowest flower). Description: Flowering stem rounded, smooth and with a dull appearance. On the stems are several (average: 8)

sheating leafy stipules, shaped broad deltoid, average length 4 mm, average width 7 mm, green color (in between RHS 137A and RHS N189A). Average number of flowers and flower buds per stem: 14. Color: Dark greyed-green, darker than RHS N189A, speckled green; RHS 137A.

Reproductive organs: Column club-shaped and appearing to be in the same (basic) color as the petals and sepals. All reproductive organs are united in the column.

*Column.*—Length: Average 9 mm. Width: Average 6 mm. Color: Purple; from RHS 77B to RHS 77D, partly very pale purple; RHS 76C to almost white.

*Pollen.*—Pollen united in two stalked pollinia (pollen masses), pollinia shaped globular, average diameter 1 mm, orange; RHS 24A.

*Stigma.*—Two stigmatic surfaces on top of the column, stigmas not stalked and unable to define as separate reproductive organs, but part of the column. Shape: The stigmatic surfaces are rounded, slightly convex. Dimension: Average diameter 2 mm, average height 0.5 mm. Color: White; RHS 155A.

*Styles.*—No styles, the column holds both pollen and stigmas (stigmatic surfaces).

*Ovary.*—Dimension: Average length 4 mm, average width 2.5 mm. Color: White; RHS 155A, flushed pink to greenish-white; RHS 157B.

*Pedicel.*—Rounded, slightly glossy. Dimension: Average length 2.8 cm, average width 3 mm. Color: Green; varying from RHS 143C to RHS 143D, the darker (RHS 143C) also visible as axillary stripes, due to resupination of flower when opening.

Seeds/fruit: No observations made.

Roots: Fleshy, rounded, slightly glossy, average diameter 5 mm, green in color, from RHS 138A to RHS 143A. Time to initiate roots is about 28 days at temperatures of 24 degrees Celsius in the summer and about 42 days in the winter. Time to produce to develop a rooted plant from a tissue-cultured plantlet is about 168 days in the summer at temperatures of 24 degrees Celsius and 270 days at the same temperature in the Winter.

Pest disease resistance/susceptibility: No observations to date.

General observations: Broad elliptic leaves; green inflorescence stem; showy light purple flowers with dark purple stripes and white margins; and dull, green leaves and purple spots; and freely flowering with 10–15 flowers and buds per raceme.

I claim:

1. A new and distinct cultivar of Phalaenopsis orchid plant named 'Isis', as illustrated and described.

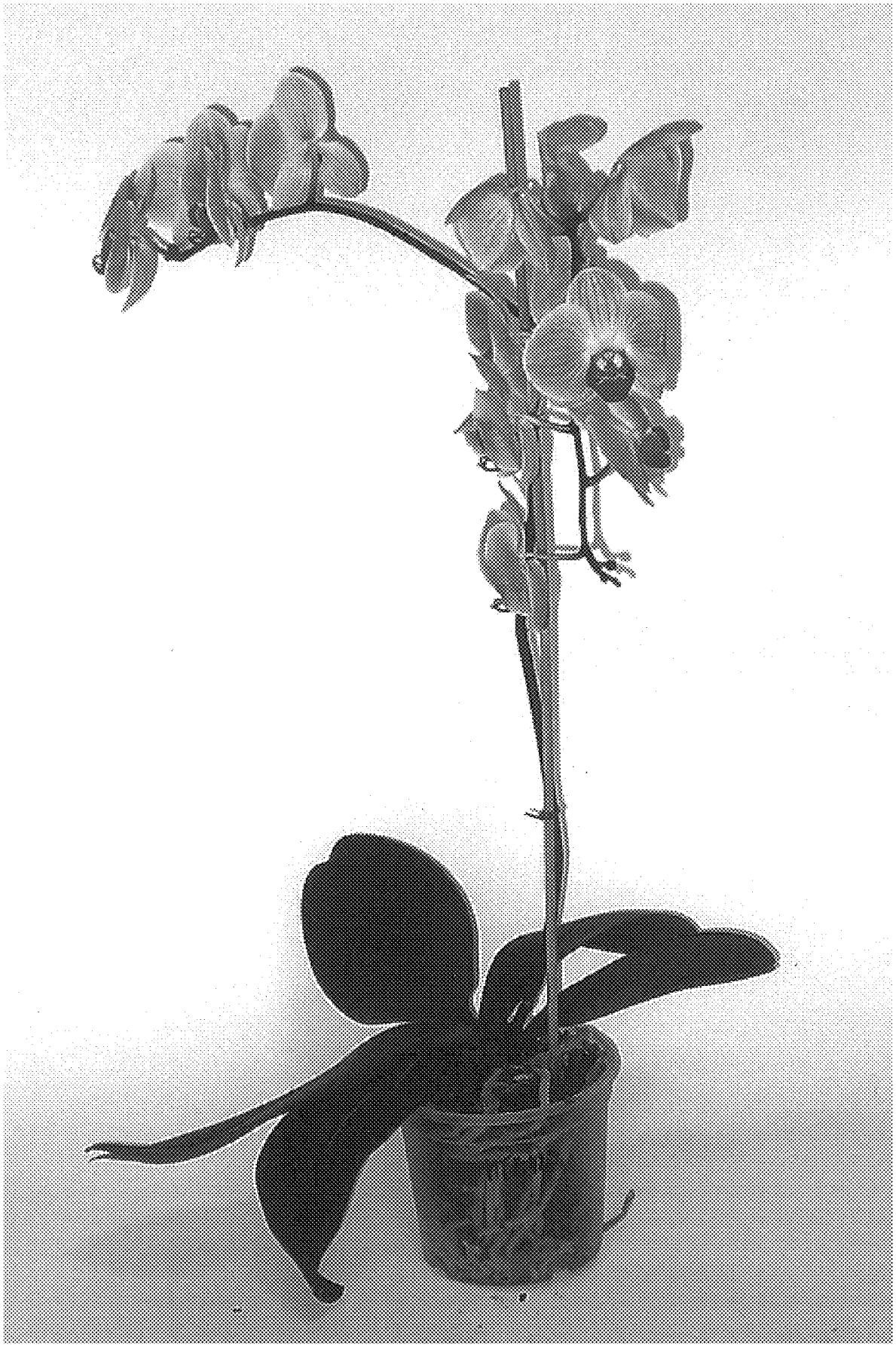

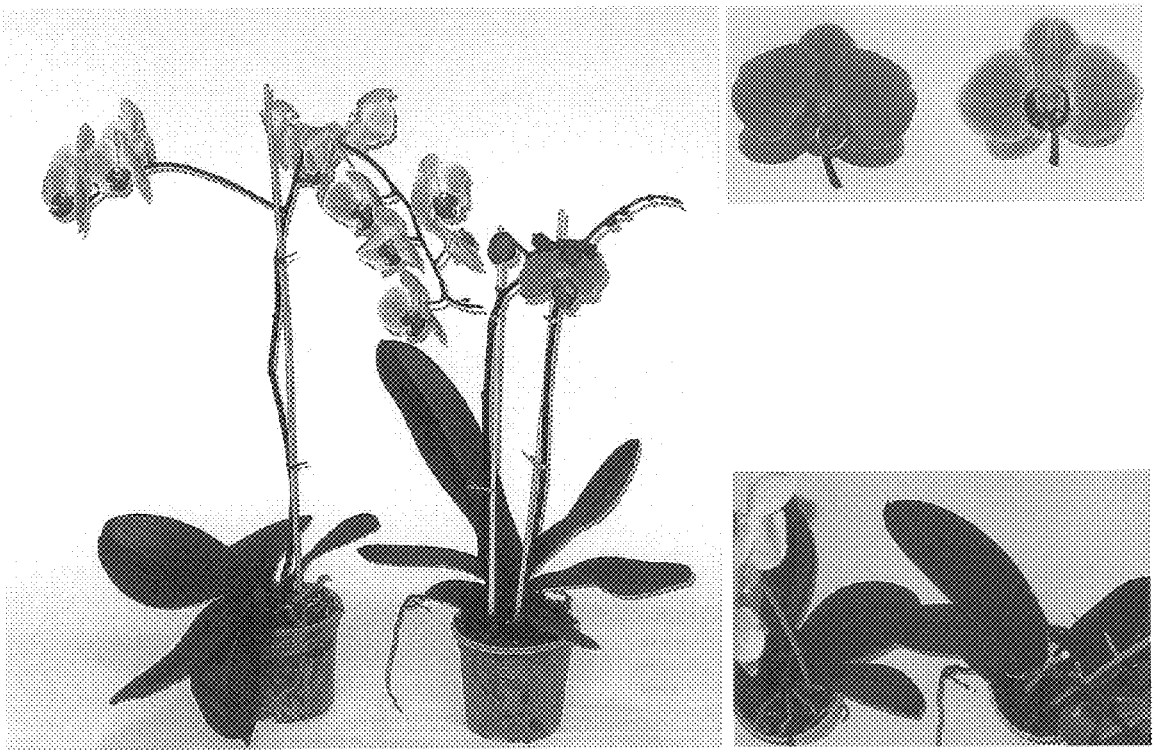

* * * * *